US005460174A

United States Patent [19]

Chang

[11] Patent Number: 5,460,174

[45] Date of Patent: Oct. 24, 1995

[54] OXYGEN SUPPLYING SYSTEM HAVING FLOW CONTROL THROTTLE

[76] Inventor: Huang Chang, 58, Ma Yuan West St., Taichung, Taiwan

[21] Appl. No.: 185,052

[22] Filed: Jan. 24, 1994

[51] Int. Cl.[6] ............................ A61M 16/00; A62B 9/02; A62B 18/02

[52] U.S. Cl. ................................ 128/204.25; 128/205.24; 128/205.25

[58] Field of Search ......................... 128/204.18, 205.22, 128/205.24, 205.25, 206.21, 206.27, 206.28, 207.11, 207.12, 204.26, 202.27, 204.27, 205.22

[56] References Cited

U.S. PATENT DOCUMENTS

| | | | |
|---|---|---|---|
| 1,310,825 | 7/1919 | Ganzer | 128/204.26 |
| 1,509,319 | 9/1924 | Saunier | 128/207.12 |
| 3,362,404 | 1/1968 | Beasley | 128/204.26 |
| 4,148,311 | 4/1979 | London et al. | 128/204.26 |
| 4,498,471 | 2/1985 | Kranz et al. | 128/204.26 |
| 4,850,345 | 7/1989 | Jackson | 128/202.27 |
| 5,052,383 | 10/1991 | Chabert | 128/205.24 |
| 5,070,872 | 12/1991 | Neuber | 128/205.24 |
| 5,092,325 | 3/1992 | Ainscaugh | 128/201.27 |
| 5,243,972 | 9/1993 | Huang | 128/205.22 |

*Primary Examiner*—Kimberly L. Asher
*Assistant Examiner*—Virendra Srivastava

[57] ABSTRACT

An oxygen supplying system includes a mask, a bottle for accommodating oxygen, an inlet pipe connecting the bottle to the inlet of the mask for supplying oxygen into the mask, and a throttle device disposed in the inlet pipe, the flowing of the oxygen is controlled to flow either intermittently or continuously by the throttle device, membranes can be disposed between the inlet pipe and an outlet pipe for sucking breathed air when when oxygen flows through the inlet pipe.

3 Claims, 8 Drawing Sheets

OXYGEN SUPPLYING SYSTEM HAVING FLOW CONTROL THROTTLE

BACKGROUND OF THE INVENTION

1. Field of the Invention

The present invention relates to a system, and more particularly to an oxygen supplying system.

2. Description of the Prior Art

Seriously polluted areas have been greatly increased, such as chemical plants, painting areas, the workers may require to use filtering devices; various kinds of filtering devices have been developed, in which, as shown in FIGS. 6 and 7, a typical filtering device is shown and comprises a filter 1 for filtering polluted air, however, the fresh air supplying rate is not fast enough such that the users may feel uncomfortable.

As shown in FIGS. 8 and 9, an oxygen supplying system is shown and comprises a bottle 2 for accommodating pressurized oxygen, and a mouthpiece or a mask 3 connected to the bottle 2 via an opening 4, however, oxygen is supplied into the mask 3 via the opening 4, and the carbon dioxide breathed out by the users is also be forced out through the opening 4, whereby, the pressure within the mask 3 will be increased such that the users may feel uncomfortable.

As shown in FIGS. 10 and 11, another type of oxygen supplying system is shown and comprises a bottle 2 for supplying pressurized oxygen into a mouthpiece or a mask 3, a buffer space 5 is provided between the bottle 2 and the mask 3 for decreasing the pressure of the oxygen, and an outlet valve 6 is provided in the mask 3 for exhaust the carbon dioxide breathed by the users, however, the users have to breathe hard in order to open the outlet valve 6, this may also increase the pressure within the mask 3.

The present invention has arisen to mitigate and/or obviate the afore-described disadvantages of the conventional oxygen supplying system.

SUMMARY OF THE INVENTION

The primary objective of the present invention is to provide an oxygen supplying system with which the users may feel comfortable.

In accordance with one aspect of the invention, there is provided an oxygen supplying system comprising a mask including an inlet and an outlet; a bottle for accommodating oxygen; a first pipe connecting the bottle to the inlet of the mask for supplying oxygen into the mask; and a throttle means disposed in the first pipe for controlling flowing of the oxygen.

The throttle means includes a body having a chamber formed therein, the chamber including two end portions, an entrance and an exit communicated with the chamber, a piston slidably disposed in the chamber, means for biasing the piston toward the entrance, a first bypass communicating the end portions of the chamber, the oxygen flows into the exit via the first bypass when the piston is forced toward the exit and when oxygen flows into the chamber.

A second bypass is further formed in the body and communicating the entrance with the exit, a button is disposed in the body for blocking the second bypass, the oxygen continuously flows through the second bypass when the second bypass is not blocked by the button.

A second pipe is further connected to the outlet of the mask, two stubs connected between the first pipe and the second pipe, two membranes disposed in the stubs respectively, the membranes being sucked toward the first pipe when the oxygen flows through the first pipe such that air in the outlet of the mask is drawn out through the second pipe.

Further objectives and advantages of the present invention will become apparent from a careful reading of the detailed description provided hereinbelow, with appropriate reference to the accompanying drawings.

DETAILED DESCRIPTION OF THE PREFERRED EMBODIMENT

Figure 1:
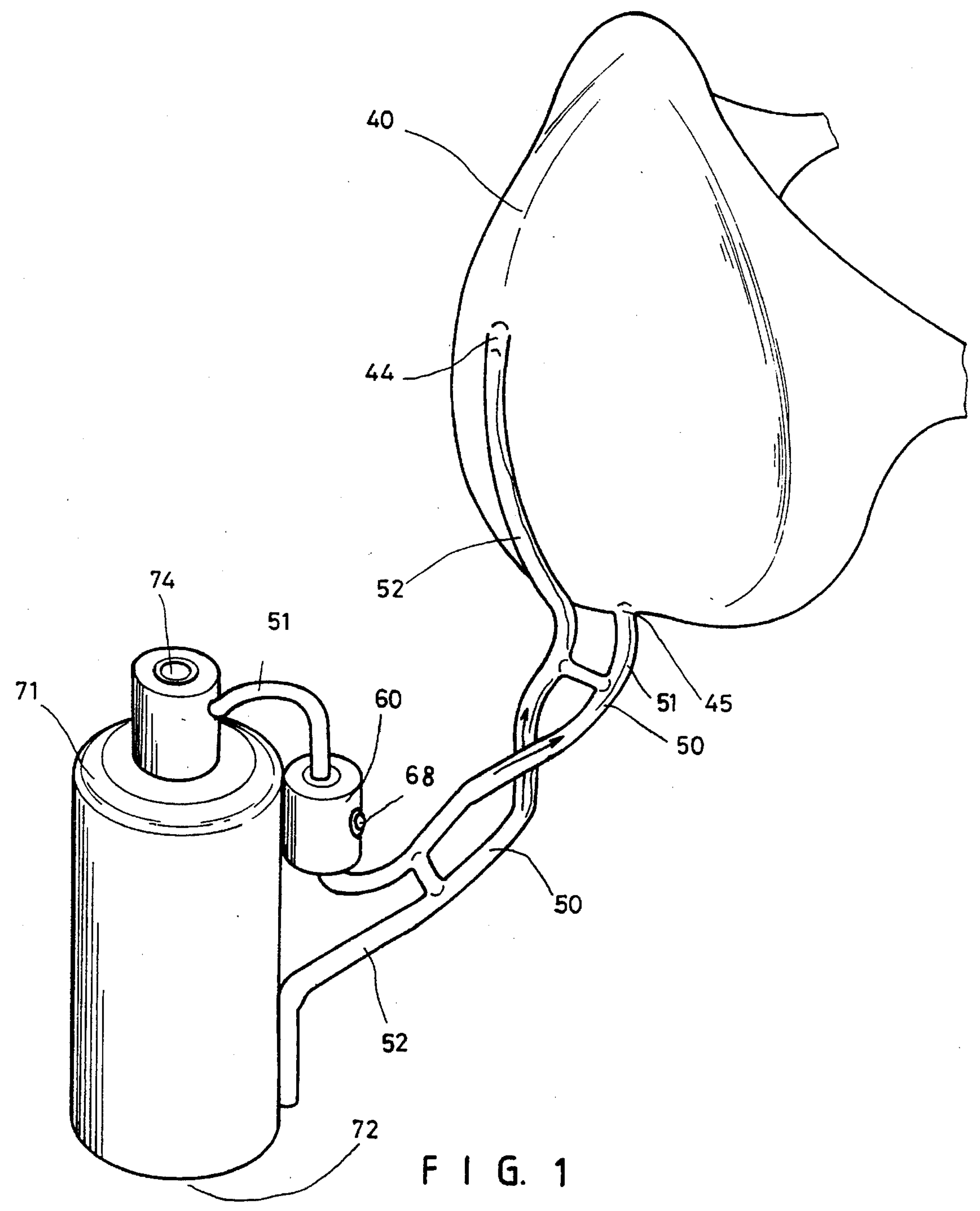
FIG. 1 is a perspective view of an oxygen supplying system in accordance with the present invention.
Figure 2:
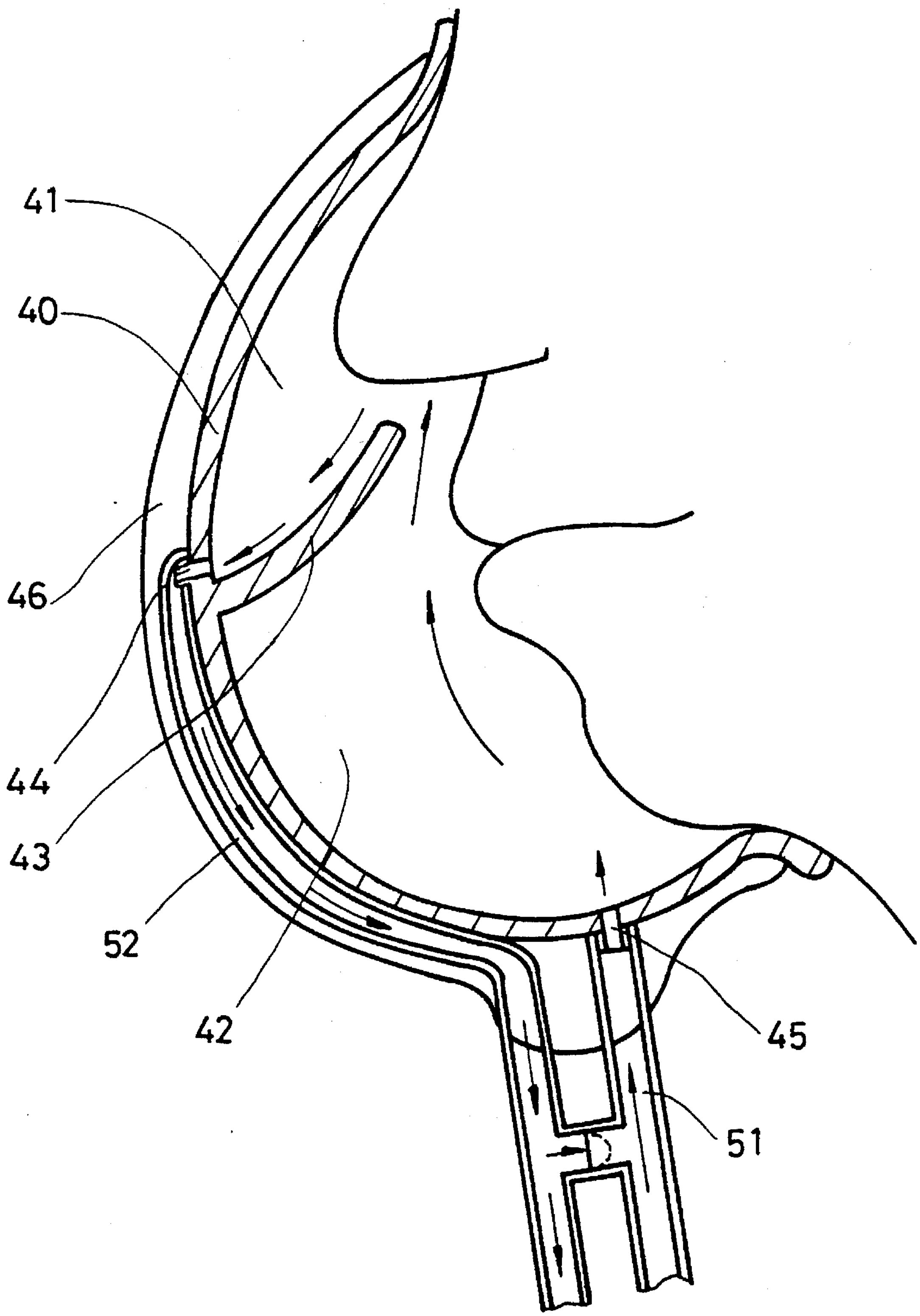
FIG. 2 is a partial cross sectional view of the oxygen supplying system.
Figure 3:
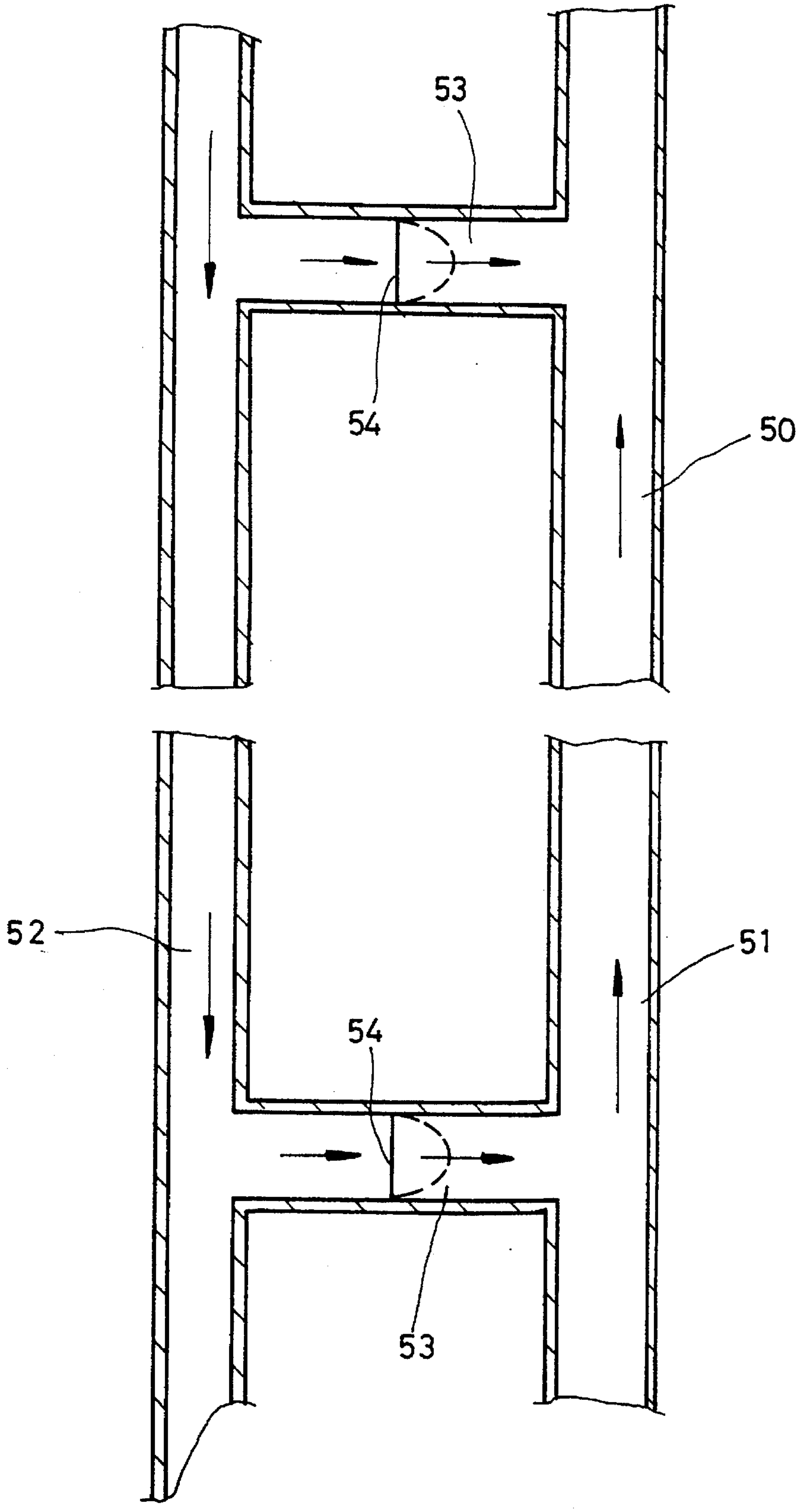
FIG. 3 is a schematic view illustrating the flowing of the air of the system.

Referring to the drawings, and initially to FIGS. 1 to 3, an oxygen supplying system in accordance with the present invention comprises a mouthpiece or a mask 40, a bottle 71 for accommodating pressurized oxygen including a bottom portion 72 provided for recharging oxygen into the bottle 71, a piping 50 for coupling the mask 40 to the bottle 71, and a throttle device 60 for controlling the flowing of the oxygen.

The mask 40 includes a partition 43 formed therein for separating the interior of the mask 40 into a first space 41 for receiving the carbon dioxide breathed by the users, and a second space 42 for receiving the oxygen from the bottle 71, an outlet 44 for exhausting the carbon dioxide, and an inlet 45 communicated with the piping 50, another cover 46 may further be provided for at least covering the outlet pipe 52. The piping 50 includes an inlet pipe 51, an outlet pipe 52 and two stubs 53 communicated between the inlet pipe 51 and the outlet pipe 52, the inlet pipe 51 has one end connected to the inlet 45 of the mask 40 and the other end secured to the bottle 71 for supplying oxygen into the mask 40, the throttle device 60 is disposed in the middle portion of the inlet pipe 51 for controlling the flowing of the oxygen, the outlet pipe 52 has one end connected to the outlet 44 of the mask 40 and the other end opened to the air for exhaust the air breathed out by the users. A membrane 54 is provided in each of the stubs 53.

Figure 4:
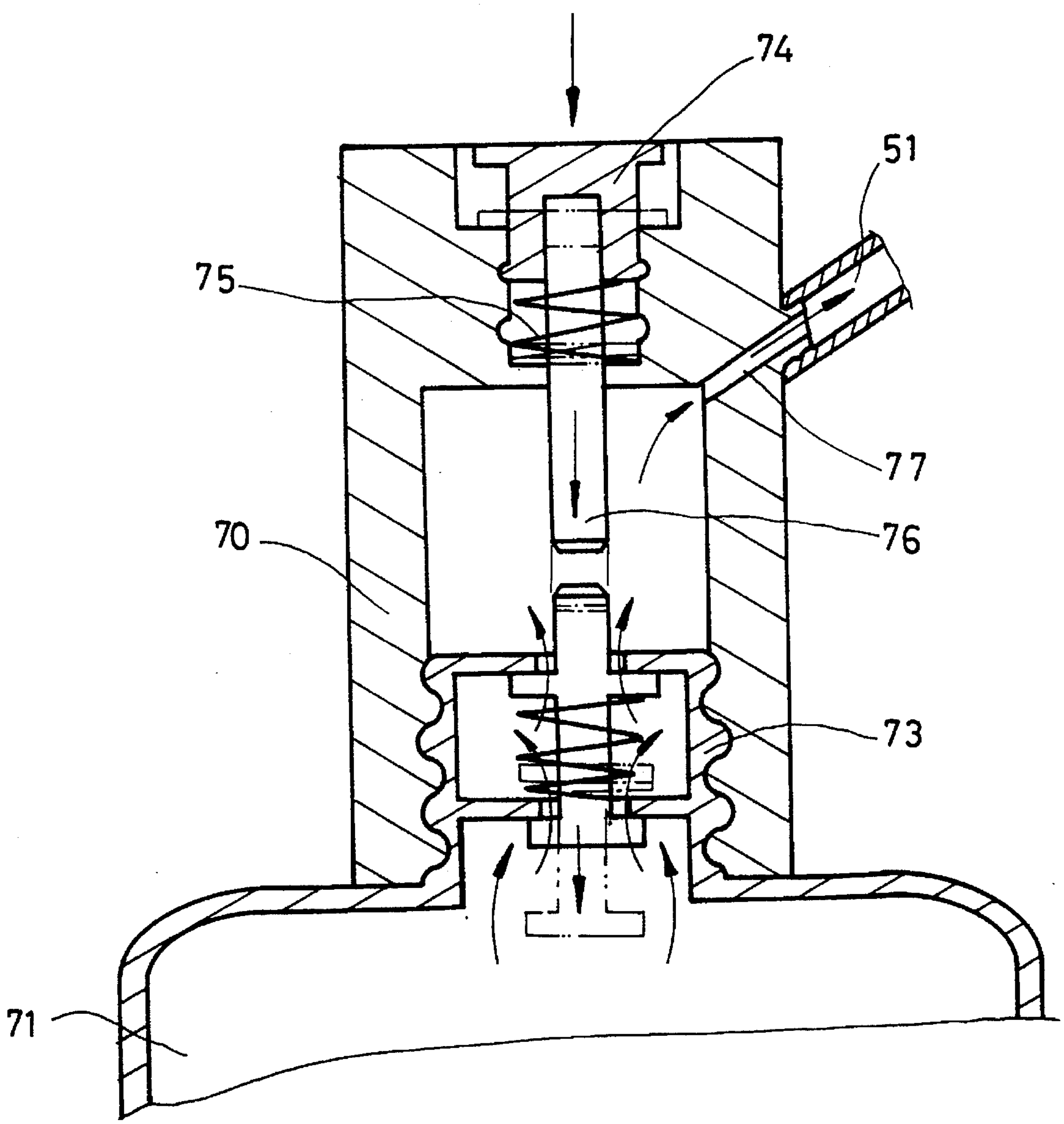
FIG. 4 is a partial cross section of the bottle.

Referring next to FIG. 4, the bottle 71 includes a mouth 73 provided in the top and having a valve disposed therein, a cap 70 threaded to the mouth 73 and including a button 74 provided in the top port ion thereof, the button 74 including a pin 76 extended downward toward the valve of the mouth 73 for actuating the valve, a spring 75 for biasing the button 74 upward, an exit 77 formed in the cap 70 and connected to the inlet pipe 51, when the valve of the mouth 73 is depressed and actuated by the pin 76 of the button 74, the pressurized oxygen accommodated in the bottle 71 is allowed to flow through the valve and to flow out through the exit 77.

Figure 5A:
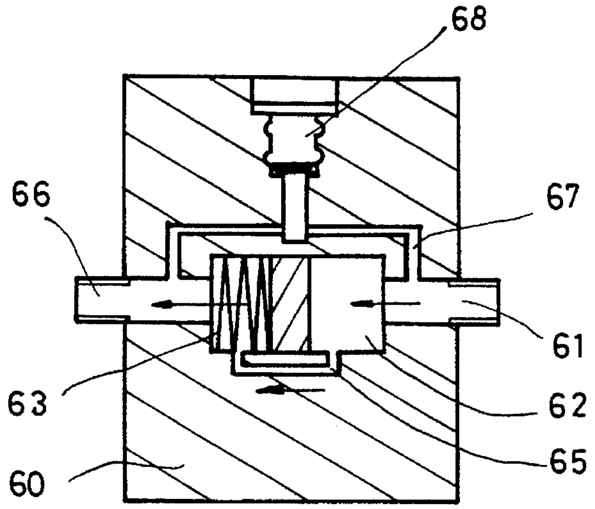
FIGS. 5A, 5B, 5C are cross sectional views showing the interior of a throttle device.
Figure 5B:
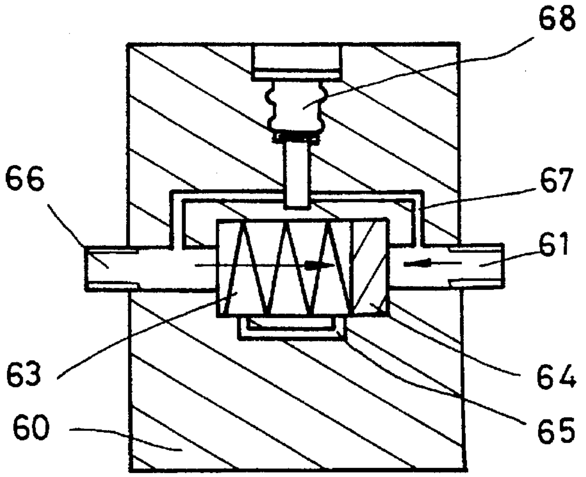
Figure 5C:
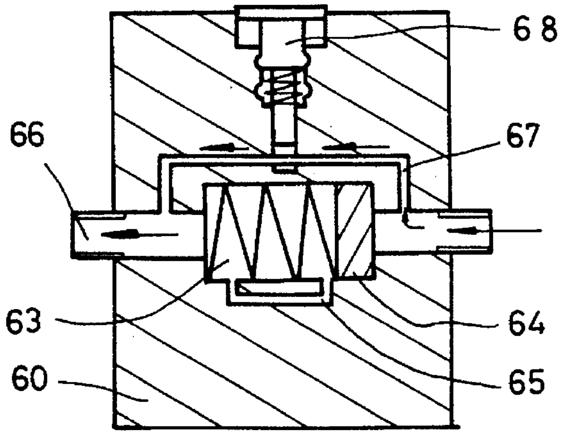
Figure 7:
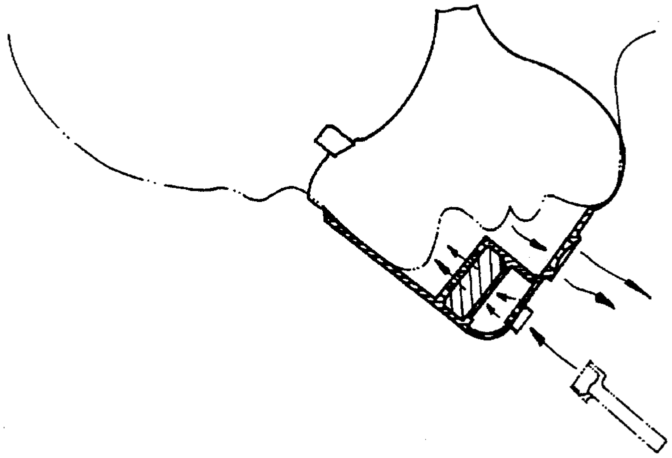
FIG. 7 PRIOR ART
FIGS. 6 and 7 are schematic views illustrating a typical oxygen supplying system.
Figure 6:
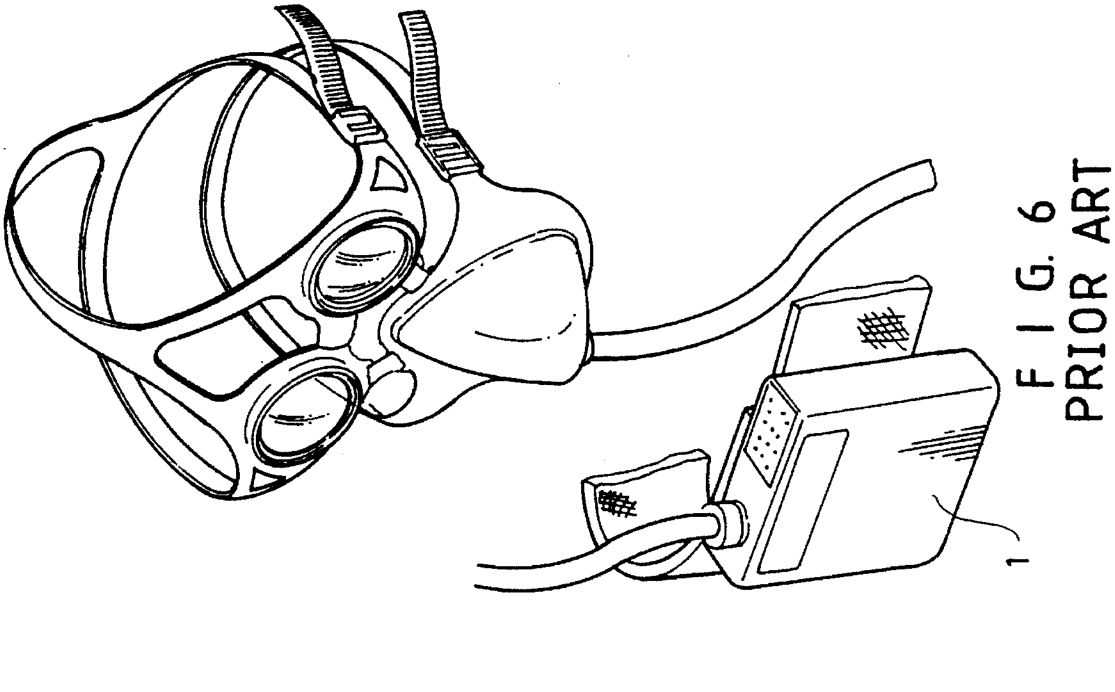
FIG. 6 PRIOR ART
Figure 9:
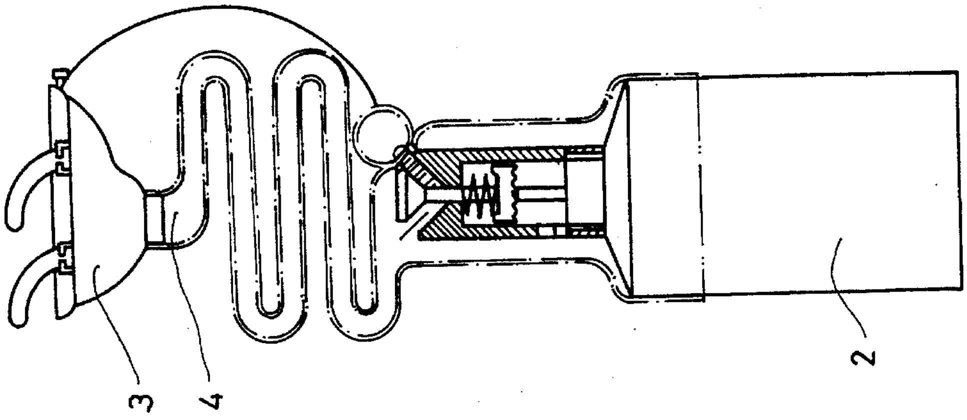
FIG. 9 PRIOR ART
FIGS. 8 and 9 are schematic views illustrating another typical oxygen supplying system.
Figure 8:
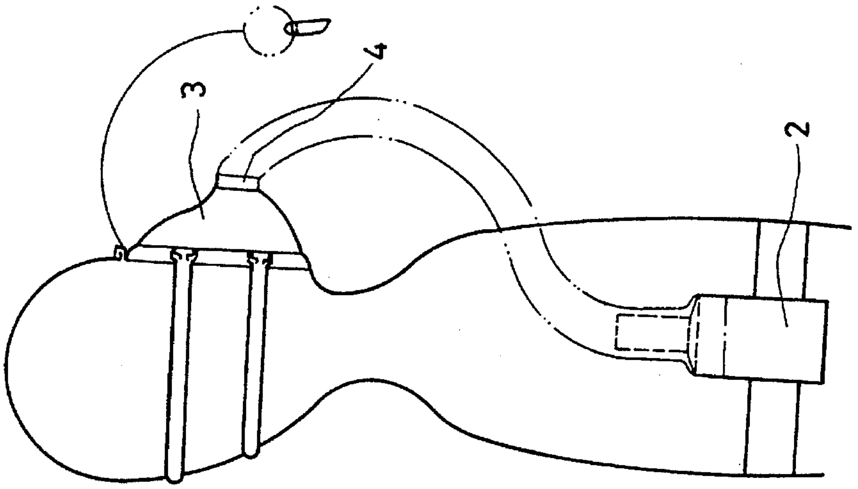
FIG. 8 PRIOR ART
Figure 10:
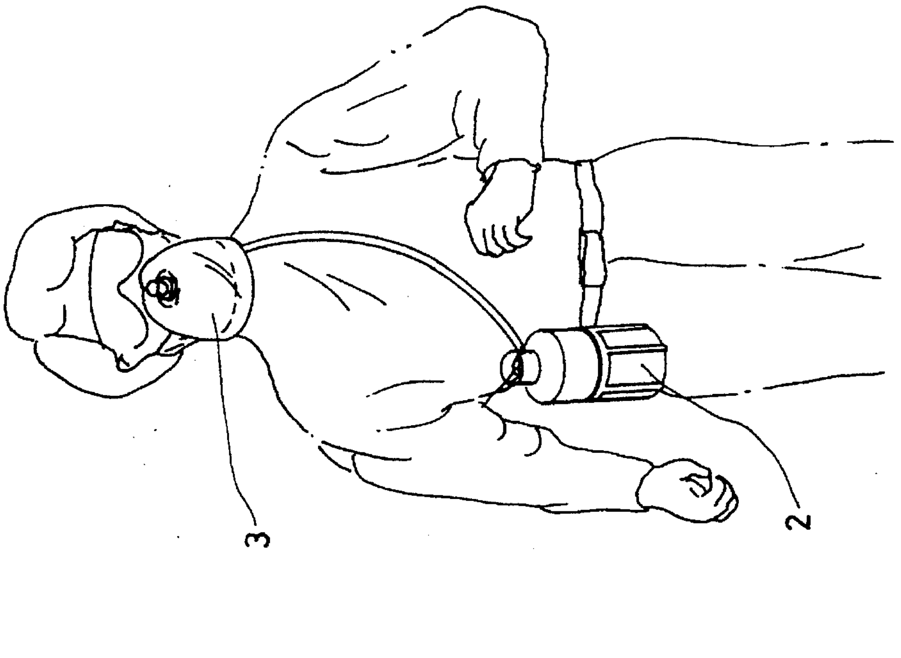
FIG. 10 PRIOR ART
FIGS. 10 and 11 are schematic views illustrating a further typical oxygen supplying system.
Figure 11:
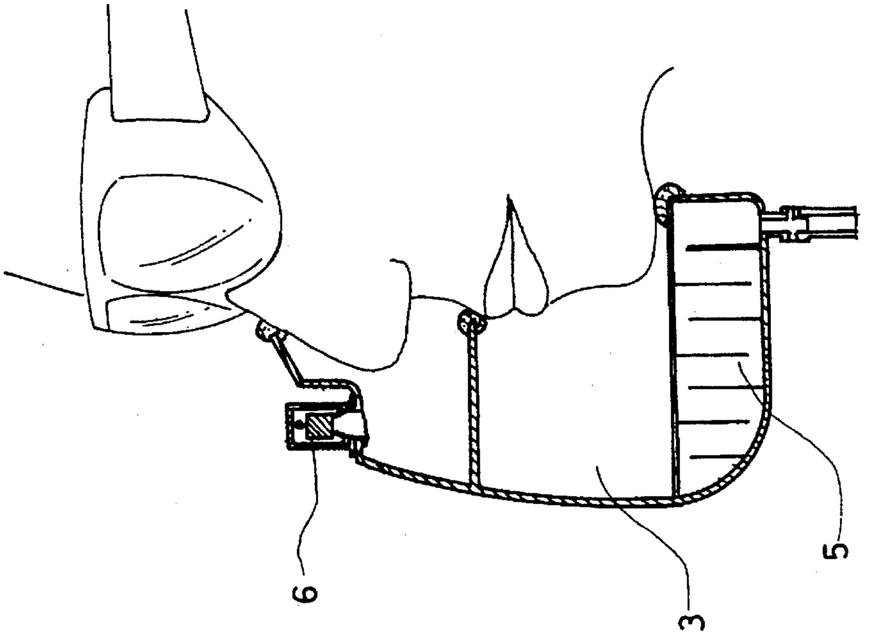
FIG. 11 PRIOR ART

Referring next to FIGS. 5A and 5B the throttle device 60 includes a chamber 62 formed therein, an entrance 61 and an exit 66 connected to the chamber 62, a piston 64 slidably received in the chamber 62, a spring 63 disposed in the chamber 62 for biasing the piston 64 toward the entrance 61, a bypass 65 formed in the throttle device 60 for communicating two end portions of the chamber 62, another bypass 67 for communicating the entrance 61 and the exit 66, and a button 68 for blocking the bypass 67. When oxygen flows into the chamber 62 via the entrance 61 from the bottle 71 and when the bypass 67 is blocked by the button 68, as shown in FIG. 5A, the piston 64 is forced toward the exit 66 against the spring 63, such that the oxygen may flow out through the exit 66 via the bypass 65, when oxygen flows through the bypass 65, the pressure in the right side of the piston 64 will be decreased and the piston 64 will be pushed toward the entrance by the spring 63 in order to block the bypass 65, then, the piston 64 can be forced toward the exit 66 again by the pressurized oxygen, such that oxygen may flow through the throttle device 60 intermittently and may flow into the mask 40. As shown in FIG. 5C, when the button 68 is released such that the bypass 67 is opened, oxygen may flow into the exit 66 via the bypass 67 and the piston 64 will not be forced toward the exit 66 such that oxygen may flow through the throttle device 60 continuously.

Referring again to FIG. 3, when oxygen flows into the mask 40 through the inlet pipe 51, the membranes 54 will be deformed and sucked toward the inlet pipe 51 due to the flowing of the oxygen, the carbon dioxide breathed out into the outlet pipe 52 by the users may be sucked through the outlet pipe 52 when the membranes 54 are sucked toward the inlet pipe 51.

Accordingly, the oxygen supplying system in accordance with the present invention includes a throttle device for supplying oxygen into the mask intermittently, and includes membrane means for sucking carbon dioxide breathed out by the users.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. An oxygen supplying system comprising:

a mask including an inlet and an outlet;

a bottle for accommodating oxygen;

a first pipe connecting said bottle to said inlet of said mask for supplying oxygen into said mask;

a throttle means disposed in said first pipe for controlling flowing of said oxygen;

a second pipe connected to said outlet of said mask, two stubs connected between said first pipe and said second pipe, two membranes disposed in said stubs respectively, said membranes being sucked toward said first pipe when said oxygen flows through said first pipe such that air in said outlet of said mask is drawn out through said second pipe.

2. An oxygen supplying system according to claim 1, wherein said throttle means includes a body having a chamber formed therein, said chamber including two end portions, an entrance and an exit communicated with said chamber, a piston slidably disposed in said chamber, means for biasing said piston toward said entrance, a first bypass communicating said end portions of said chamber, said oxygen flows into said exit via said first bypass when said piston is forced toward said exit and when oxygen flows into said chamber.

3. An oxygen supplying system according to claim 2, wherein a second bypass is formed in said body and communicating said entrance with said exit, a button is disposed in said body for blocking said second bypass, said oxygen continuously flows through said second bypass when said second bypass is not blocked by said button.

* * * * *